United States Patent
Zhu et al.

(10) Patent No.: US 9,395,374 B2
(45) Date of Patent: *Jul. 19, 2016

(54) ANALYSIS OF AMINO ACID COPOLYMER COMPOSITIONS

(71) Applicant: Momenta Pharmaceuticals, Inc., Cambridge, MA (US)

(72) Inventors: Xiangping Zhu, Acton, MA (US); Zachary Shriver, Cambridge, MA (US); Yanjie Jiang, Cambridge, MA (US); Corinne Bauer, Cambridge, MA (US); James Eric Anderson, Cambridge, MA (US); Peter James Ahern, Cambridge, MA (US)

(73) Assignee: Momenta Pharmaceuticals, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/795,867

(22) Filed: Jul. 9, 2015

(65) Prior Publication Data

US 2015/0376334 A1 Dec. 31, 2015

Related U.S. Application Data (63) Continuation of application No. 14/019,119, filed on Sep. 5, 2013, now Pat. No. 9,085,796, which is a continuation of application No. 13/709,586, filed on Dec. 10, 2012, now Pat. No. 8,592,142, which is a continuation of application No. 12/408,058, filed on Mar. 20, 2009, now Pat. No. 8,329,391.

(60) Provisional application No. 61/045,465, filed on Apr. 16, 2008.

(51) Int. Cl.
| | |
|---|---|
| A61K 38/02 | (2006.01) |
| G01N 33/68 | (2006.01) |
| C07K 14/00 | (2006.01) |
| C12Q 1/37 | (2006.01) |
| C08G 69/10 | (2006.01) |
| A61K 31/785 | (2006.01) |

(52) U.S. Cl.
CPC .......... *G01N 33/6812* (2013.01); *A61K 31/785* (2013.01); *A61K 38/02* (2013.01); *C07K 14/001* (2013.01); *C08G 69/10* (2013.01); *C12Q 1/37* (2013.01)

(58) Field of Classification Search
None
See application file for complete search history.

(56) References Cited

U.S. PATENT DOCUMENTS

| | | | |
|---|---|---|---|
| 3,849,550 A | 11/1974 | Teitelbaum et al. | |
| 5,112,810 A | 5/1992 | Nagai et al. | |
| 5,800,808 A | 9/1998 | Konfino et al. | |
| 5,981,589 A | 11/1999 | Konfino et al. | |
| 6,048,898 A | 4/2000 | Konfino et al. | |
| 6,054,430 A | 4/2000 | Konfino et al. | |
| 6,291,310 B1 | 9/2001 | Madson et al. | |
| 6,342,476 B1 * | 1/2002 | Konfino ............ | A61K 38/1703 424/78.37 |
| 6,362,161 B1 | 3/2002 | Konfino et al. | |
| 6,514,938 B1 | 2/2003 | Gad et al. | |
| 6,620,847 B2 | 9/2003 | Konfino et al. | |
| 6,800,287 B2 | 10/2004 | Gad et al. | |
| 6,821,745 B2 | 11/2004 | Smith | |
| 6,844,314 B2 | 1/2005 | Eisenbach-Schwartz et al. | |
| 6,939,539 B2 | 9/2005 | Konfino et al. | |
| 7,033,582 B2 | 4/2006 | Yong et al. | |
| 7,041,472 B2 | 5/2006 | Norioka et al. | |
| 7,049,399 B2 | 5/2006 | Bejan et al. | |
| 7,053,043 B1 | 5/2006 | Aharoni et al. | |
| 7,074,580 B2 | 7/2006 | Gad et al. | |
| 7,199,098 B2 | 4/2007 | Konfino et al. | |
| 7,329,353 B2 | 2/2008 | Dillon et al. | |
| 7,427,600 B2 | 9/2008 | Mickle et al. | |
| 7,495,072 B2 | 2/2009 | Dolitzky | |
| 7,732,162 B2 | 6/2010 | Hoffman et al. | |
| 7,884,187 B2 * | 2/2011 | Zhu ...................... | C07K 14/001 530/344 |
| 8,058,235 B1 | 11/2011 | Coleman et al. | |
| 8,329,391 B2 * | 12/2012 | Zhu ...................... | C07K 14/001 435/23 |
| 8,592,142 B2 * | 11/2013 | Zhu ...................... | C07K 14/001 435/23 |
| 8,859,489 B2 | 10/2014 | Coleman | |
| 9,085,796 B2 * | 7/2015 | Zhu ...................... | C07K 14/001 |
| 2001/0023960 A1 | 9/2001 | Soga et al. | |
| 2002/0115103 A1 | 8/2002 | Gad et al. | |
| 2003/0064914 A1 | 4/2003 | Konfino et al. | |
| 2003/0153007 A1 | 8/2003 | Chen et al. | |
| 2003/0170729 A1 | 9/2003 | Klinger | |
| 2004/0091956 A1 | 5/2004 | Bejan et al. | |
| 2004/0106554 A1 | 6/2004 | Konfino et al. | |

(Continued)

FOREIGN PATENT DOCUMENTS

| | | |
|---|---|---|
| CA | 2 411 786 | 5/2004 |
| CA | 2 767 919 | 5/2006 |

(Continued)

OTHER PUBLICATIONS

Suzuki et al. ("Quantitative Analysis of Pyroglutamic Acid in Peptides" J. Agric. Food Chem. 1999, 47, 3248-3251).*

(Continued)

*Primary Examiner* — Christina Bradley
(74) *Attorney, Agent, or Firm* — Fish & Richardson P.C.

(57) ABSTRACT

Methods for analyzing, selecting, characterizing or classifying compositions of a co-polymer, e.g., glatiramer acetate are described. The methods entail analysis of pyro-glutamate in the composition, and, in some methods, comparing the amount of pyro-glutamate present in a composition to a reference standard.

14 Claims, 3 Drawing Sheets

(56) References Cited

U.S. PATENT DOCUMENTS

| | | |
|---|---|---|
| 2005/0038233 A1 | 2/2005 | Gad et al. |
| 2005/0171286 A1 | 8/2005 | Konfino et al. |
| 2006/0052586 A1 | 3/2006 | Dolitzky |
| 2006/0058225 A1 | 3/2006 | David et al. |
| 2006/0154862 A1 | 7/2006 | Ray et al. |
| 2006/0172942 A1 | 8/2006 | Dolitzky |
| 2007/0021324 A1 | 1/2007 | Dolitzky |
| 2007/0141663 A1 | 6/2007 | Ding et al. |
| 2007/0148979 A1 | 6/2007 | Lee et al. |
| 2007/0161566 A1 | 7/2007 | Pinchasi |
| 2007/0178113 A1 | 8/2007 | Backstrom et al. |
| 2008/0003791 A1 | 1/2008 | Cho et al. |
| 2008/0220441 A1 | 9/2008 | Birnbaum et al. |
| 2008/0254639 A1 | 10/2008 | Graff |
| 2008/0319092 A1 | 12/2008 | Singh |
| 2009/0011108 A1 | 1/2009 | Kogiso et al. |
| 2009/0035816 A1 | 2/2009 | Chan et al. |
| 2009/0099130 A1 | 4/2009 | Demetriou et al. |
| 2009/0176342 A1 | 7/2009 | Lee et al. |
| 2009/0263347 A1 | 10/2009 | Jiang et al. |
| 2010/0036092 A1 | 2/2010 | Hsiao et al. |
| 2010/0040537 A1 | 2/2010 | Gu et al. |
| 2010/0111952 A1 | 5/2010 | Beckman et al. |
| 2010/0234566 A1 | 9/2010 | Ray et al. |
| 2010/0256039 A1 | 10/2010 | Coleman et al. |
| 2010/0285513 A1 | 11/2010 | Chan et al. |
| 2010/0324265 A1 | 12/2010 | Kota et al. |
| 2011/0183426 A1 | 7/2011 | Chan et al. |
| 2011/0269690 A1 | 11/2011 | Coleman et al. |
| 2013/0095515 A1 | 4/2013 | Zhu et al. |
| 2014/0065652 A1 | 3/2014 | Zhu et al. |
| 2015/0105535 A1 | 4/2015 | Coleman et al. |

FOREIGN PATENT DOCUMENTS

| | | |
|---|---|---|
| EP | 1 408 066 | 4/2004 |
| EP | 1 878 350 | 1/2008 |
| EP | 1 807 467 | 8/2009 |
| JP | 2004/140039 | 5/2004 |
| JP | 2008/016838 | 1/2008 |
| KR | 100695500 | 3/2007 |
| KR | 1020080001881 | 1/2008 |
| WO | WO 95/31990 | 11/1995 |
| WO | WO 96/32119 | 10/1996 |
| WO | WO 00/05250 | 2/2000 |
| WO | WO 03/048735 | 6/2003 |
| WO | WO 2004/043995 | 5/2004 |
| WO | WO 2006/029393 | 3/2006 |
| WO | WO 2006/029411 | 3/2006 |
| WO | WO 2006/050122 | 5/2006 |
| WO | WO 2006/069739 | 7/2006 |
| WO | WO 2006/069765 | 7/2006 |
| WO | WO 2006/083608 | 8/2006 |
| WO | WO 2006/118090 | 11/2006 |
| WO | WO 2007/022193 | 2/2007 |
| WO | WO 2007/030573 | 3/2007 |
| WO | WO 2007/127977 | 11/2007 |
| WO | WO 2007/146331 | 12/2007 |
| WO | WO 2009/016643 | 2/2009 |
| WO | WO 2009/129018 | 10/2009 |
| WO | WO 2010/017292 | 11/2010 |
| WO | WO 2010/140157 | 12/2010 |

OTHER PUBLICATIONS

"Full Prescribing Information for Copaxone (glatiramer acetate)", Feb. 2009, retrieved from http://www.accessdata.fda.gov/drugsatfda_docs/label/2009/020622s057lbl.pdf on Dec. 30, 2013 (22 pages total).*

Abraham and Podell, 1981, Molecular and Cellular Biochemistry 38: 181-190.

Abdelaziz et al, "Inhibition of TNF-alpha production in THP-1 macrophages by glatiramer acetate does not alter their susceptibility to infection by Listeria monocytogenes and does not impair the efficacy of ampicillin or moxifloxacin against intracellular bacteria," J. Anitmicrobial Chem. 54(1):288-289, 2004.

Arnon et al., "The chemistry of the Copaxone drug," STN International, 1999 (abstract only).

Aventis Pharmaceuticals, Inc., National Drug Code (NDC) 0088-1153-30 (Copaxone®) Label Version 1 (Published Jul. 25, 2006).

Beck et al., "Stability and CTL activity of N-terminal glutamic acid containing peptides," J. Peptide Res., 2001, 57:528-538.

Beyerman et al., 1973, Proceedings of the Eleventh European Peptide Symposium, Vienna, Austria, Apr. 1971, 162-164.

Bichsel et al., "Requirements for the quality control of chemically synthesized peptides and biotechnologically produced proteins," Pharrnaceutica Acta Helvetiae, 1996, 71:439-446.

Blanchette et al., "Glatiramer acetate: evidence for a dual mechanism of action," J Neurol (2008) 255(Supp 1):26-36.

Boerner et al. "Defining Your Product Profile and Maintaining Control Over It, Part 3" BioProcess International, pp. 50-56, Oct. 2005 (5 pages total).

Bogunovic et al., "Comparative Quantitative Mass Spectrometry Analysis of MHC Class II-Associated Peptides Reveals a Role of GILT in Formation of Self-Peptide Repertoire," PLoS ONE 5(5):e10599 (2010) http://www.plosone.org/article/info%3Adoi%2F10.1371%2Fjournal.pone.0010599.

Brochure for 33% Hydrobromic Acid in Acetic Acid, Albemarle Corporation, 1999, 2 pages.

Busby et al., "An Enzyme(s) That Converts Glutaminyl-peptides into Pyroglutamyl-peptides," The Journal of Biological Chemistry, The American Society of Biological Chemists, Inc., 262(18):8532-8536 (1987).

Chelius et al. "Formation of Pyroglutamic Acid from N-Terminal Glutamic Acid in Immunoglobulin Gamma Antibodies" Anal Chem. 2006, 78, 2370-2376.

Chirino & Mire-Sluis, "Characterizing biological products and assessing comparability following manufacturing changes," Nature Biotechnology, Nov. 2004, 22(11):1383-1391.

Chiu, "Guidance for Industry for the Submission of Chemistry, Manufacturing, and Controls Information for Synthetic Peptide Substances," Center for Drug Evaluation and Research, Nov. 1994, 16 pages.

'Citizen's Petition' filed at the US Food & Drug Administration by the pharmaceutical company, Teva, Sep. 26, 2008.

Deming, Timothy J., "Synthetic polypeptides for biomedical applications," Progress in Polymer Science (Aug.-Sep. 2007) 32(8-9):858-875.

Dick et al., "Determination of the Origin of the N-Terminal Pyro-Glutamate Variation in Monoclonal Antibodies Using Model Peptides," Biotech. Bioeng., Jun. 2007, 97:544-552.

Domon and Aebersold, "Mass Spectrometry and Protein Analysis," Science, Apr. 2006, 312:212-217.

EMPROVE® Phenol: Extra Pure Phenol, USP, Ph Eur from EMD Millipore, dated Jun. 4, 2014, 2 pages.

European Medicines Agency, ICH Topic Q6 B, Specifications: Test Procedures and Acceptance Criteria for Biotechnological/Biological Products (Sep. 1999), 17 pages, retrieved from http://www.ema.europa.eu on Dec. 12, 2011.

Experimental Report by Petr Krajcovic, Synthon BV, dated Jun. 10, 2015, 2 pages.

Expert Opinion of Professor Rob M. J. Liskamp, dated Jun. 9, 2015, 13 pages.

Express Search, Inc., Accelerated Examination Search Letter for U.S. Appl. No. 12/882,790, now U.S. Pat. No. 7,884,187, Jun. 19, 2010, 7 pages.

Farina et al., "Treatment of multiple sclerosis with Copaxone (COP): Elispot assay detects COP-induced interleukin-4 and interferon-gamma response in blood cells," Brain 124(4):705-719, 2001.

Feinberg and Merrifield, 1975, J. Am. Chem. Soc., 97, 3485-3496.

Gaunt et al., 1998, J. Org. Chem. 63: 4172-4173.

Gawlik et al., "Autocatalytic Activation of the Furin Zymogen Requires Removal of the Emerging Enzyme's N-Terminus from the Active Site," PLoS ONE 4(4):e5031 (2009) http://www.plosone.org/article/info%3Adoi%2F10.1371%2Fjournal.pone.0005031.

Grimmelikhuujzen et al., "Isolation of <Glu-Gly-Arg-Phe-NH2 (AnthoRFamide), a neuropeptide from sea anemones (coelenterate/

(56) References Cited

OTHER PUBLICATIONS neurotransmitter/evolution/radioimmunoassay/HPLC)," Procedures of the National Academy of Science, USA, 83:9817-9821 (1986).
Hartmann et al., 1981, BioSystems 13: 141-147.
Hartmann J. et al., "Formation of specific amino acid sequences during carbodiimide-mediated condensation of amino acids in aqueous solution, and computer-simulated sequence generation," Origins of Life, 14, (1-4): 213-220, 1984.
Hashimoto, 1992, Bull. Chem. Soc. Jpn., 65, 1268-1274.
Hirschmann et al., "Controlled synthesis of peptides in aqueous medium. VIII. Preparation and use of novel .alpha.-amino acid N-carboxyanhydrides," J Am Chem Soc (1971) 93(11):2746-2754.
Holladay J E et al. "Catalytic Hydrogenation of Glutamic Acid" Applied Biochemistry and Biotechnology, 113-116:00. 857-869 (2004).
Jakubke and Jeschkeit (ed.), 1982, Aminosauren, Peptide, Proteine. Verlag Chemie, p. 138-14 (with English translation).
Jakubke and Sewald (ed.), 2008, Peptides from A-Z. A concise encyclopedia. ISBN 978-3-527-31722-6, p. 317 (with English abstract).
Katchalski et al., "Synthesis and Chemical Properties of Poly-α-Amino Acids," Advances in Protein Chem, Academic Press Inc., 1958, 13:243-492.
Kozlowski and Swann, "Current and future issues in the manufacturing and development of monoclonal antibodies," Advanced Drug Delivery Reviews, Aug. 2006, 58:707-722.
Li Q Q et al., "Glatiramer acetate inhibition of tumor necrosis factor-alpha-induced RANTES expression and release from U-251 MG human astrocytic cells," J. of Neurochem. 77(5):1208-1217, 2001.
Liu et al., "Characterization of the stability of a fully human monoclonal IgG after prolonged incubation at elevated temperature", Journal of Chromatography, 2006, B 837:35-43.
Masha Fridkis-Hareli, et al., 1999, Journal of Immunology 162, 4697-4704.
Material Safety Data Sheet for Hydrobromic Acid 33-35%, in Acetic Acid; http://fscimage.fishersci.com/msds/40066.htm; retrieved Apr. 13, 2011.
Milo et al., "Additive effects of copolymer-1 and interferon beta-1b on the immune response to myelin basic protein," J. of Neuroimmunology 61(2):185-193, 1995.
Moorhouse et al. "Validation of an HPLC method for the analysis of the charge heterogeneity of the recombinant monoclonal antibody I DEC-C2B8 after papain digestion" Journal of Pharmaceutical and Biomedical Analysis 16 (1997) 593-603.
Mozdzanowski et al., 1998, Anal Biochem., 260; 183-187.
Munton et al., "Qualitative and Quantitative Analyses of Protein Phosphorylation in Naïve and Stimulated Mouse Synaptosomal Preparations," American Society for Biochemistry and Molecular Biology, Brain Research Institute, Molecular & Cellular Proteomics, 6.2 (2006) Zurich Switzerland (http://www.mcponline.org/content/6/2/283.full).
Notice of Opposition Against European Patent EP2414384, Oct. 6, 2015, 18 pages.
Notice of Opposition Against European Patent EP2414384B, Oct. 6, 2015, 19 pages.
Opposition filed in corresponding European application 2 277 050 by Actavis Group ehf, dated Sep. 8, 2014, 35 pgs.
Opposition filed in corresponding European application 2 277 050 by Guardian IP Consulting I/S dated Sep. 17, 2014, 33 pgs.
Opposition filed in corresponding European application 2 277 050 by Generics [UK] Ltd (trading as Mylan) dated Oct. 9, 2014, 17 pgs.
Ozols, "Isolation and the complete amino acid sequence of luminal endoplasmic reticulum glucose-6-phosphate dehydrogenase," Procedures of the National Academy of Science, USA, 90:5302-5306 (1993).
Park et al., "L-Pyroglutamate Spontaneously Formed from L-Glutamate Inhibits Growth of the Hyperthermophilic Archaeon Sulfolobus solfataricus," Applied and Environmental Microbiology, 67:3650-3654 (2001).
Qu et al., "Rapid determination of underivatized pyroglutamic acid, glutamic acid, glutamine and other relevant amino acids in fermentation media by LC-MS-MS," The Royal Society of Chemistry, Analyst (2002) http://www.rsc.org/delivery/_ArticleLinking/DisplayArticleForFree.cfm?doi=b108422b&JournalCode=AN.
Response to Oppositions filed in corresponding European application 2 277 050 by Momenta Pharmaceuticals, dated Apr. 15, 2015, 52 pages.
Rudinger et al., 1959, Amino Acids and Peptides, XXVI, 24, 2013-2017.
Schechter et al., "Synthetic antigens with sequential and conformation-dependent determinants containing the same L-tyrosyl-L-alanyl-L-glutamyl sequence," Eur J Biochem (1971) 20:309-320.
Sela et al., "Studies on the chemical basis of the antigenicity of proteins, 5. Synthesis, characterization and immunogenicity of some multichain and linear polypeptides containing tyrosine," Biochem J (1962) 85:223-235.
Sorup et al., "Physicochemical studies of a branched polypeptide antigen: poly(l-Tyr,l-Glu)-poly(dl-Ala)-poly(l-Lys)," Biochimica et Biophysica Acta (BBA)—Protein Structure (Sep. 27, 1977) 494(1):9-18.
Tarcic et al., "Copolymer 1 (Copaxone) from an idea to drug for treatment of multiple sclerosis", vol. 28, pp. 14, 16-18, Journal; General Review, 1997, CODEN: KHKIEZ, ISSN: 0792-609X.
Teitelbaum et al., "Copaxone," Comprehensive Medicinal Chemistry II (2007) 8: 173-185.
Teitelbaum et al., "Suppression of Experimental Allergic Encephalomyelitis by a Snythetic Polypeptide," Eur. J. Immunol , 1971, 1:242-248.
Third Party Observation in European Patent EP2414384, dated Jun. 10, 2014, 4 pages.
Third Party Observation in European Patent Application No. 10715379.3, dated Dec. 23, 2013, 8 pages.
U.S. Appl. No. 60/608,843, filed Sep. 9, 2004, priority document for PCT Application No. PCT/US2005/032395, 42 pages.
Varkony et al., "The glatiramoid class of immunomodulator drugs," Expert Opin. Pharmacother., Mar. 2009, 10:(4)657-668.
Yang et al., "Drug Acyl Glucuronides: Reactivity and Analytical Implication," Curr. Pharmac. Analysis (Netherlands) 2(3):259-277, 2006.
Yu, et al., "Investigation of N-terminal glutamate cyclization of recombinant monoclonal antibody in formulation development," Journal of Pharmaceutical and Biomedical Analysis, 2006, 42:455-463.

* cited by examiner

ANALYSIS OF AMINO ACID COPOLYMER COMPOSITIONS

RELATED APPLICATION INFORMATION

This application is a continuation of U.S. patent application Ser. No. 14/019,119, filed Sep. 5, 2013, which is a continuation of U.S. patent application Ser. No. 13/709,586, filed Dec. 10, 2012, which is a continuation of U.S. patent application Ser. No. 12/408,058, filed Mar. 20, 2009, and claims priority to U.S. Provisional Application Ser. No. 61/045,465, filed Apr. 16, 2008. The entire disclosures of the prior applications are considered part of, and are incorporated by reference in their entireties in, the disclosure of this application.

BACKGROUND

Glatiramer acetate (also known as copolymer-1 and marketed as the active ingredient in COPAXONE® by Teva Pharmaceutical Industries Ltd., Israel) is used in the treatment of the relapsing-remitting form of multiple sclerosis (RRMS). According to the COPAXONE® product label, glatiramer acetate (GA) consists of the acetate salts of synthetic polypeptides, containing four naturally occurring amino acids: L-glutamic acid, L-alanine, L-tyrosine, and L-lysine with a reported average molar fraction of 0.141, 0.427, 0.095, and 0.338, respectively. Chemically, glatiramer acetate is designated L-glutamic acid polymer with L-alanine, L-lysine and L-tyrosine, acetate (salt). Its structural formula is:

(Glu,Ala,Lys,Tyr)$_x$·xCH$_3$COOH
(C$_5$H$_9$NO$_4$·C$_3$H$_7$NO$_2$·C$_6$H$_{14}$N$_2$O$_2$·C$_9$H$_{11}$NO$_3$)$_x$·xC$_2$H$_4$O$_2$         CAS-147245-92-9

SUMMARY OF THE INVENTION

The invention is based, at least in part, on the identification and characterization of L-pyroGlutamic Acid (gyro-Glu) as a structural signature of glatiramer acetate (GA). Analysis of this signature component of GA is useful to assess product and process quality in the manufacture of GA.

Described herein is a method of selecting a batch of a composition comprising an amino acid copolymer (e.g., GA), the method comprising: providing a batch of a composition comprising an amino acid copolymer; measuring the amount of gyro-glutamate (pyro-Glu) in the batch; and selecting the batch if the amount of pyro-Glu in the batch is within a predetermined range. In this method, as in the other methods described herein, the measuring step can employ any suitable method and the units used to express the measured amount of pyro-Glu can be any suitable units (e.g., ppm or mole percent of chains). In measuring the amount of pyro-Glu, one can, e.g., measure the concentration of pyroGlu in a sample or the total amount of pyro-Glu in sample. However an amount of pyro-Glu is measured and whatever units are used to express the measured amount, the concentration of pyro-Glu in the selected batch is between 2000 and 7000 ppm (in some cases between 2500 and 6500 ppm) on a dry weight/dry weight basis.

Also described is a method for preparing a pharmaceutical composition comprising: providing a batch of a composition comprising an amino acid copolymer, measuring the amount of pyro-Glu in the batch; and preparing a pharmaceutical composition comprising at least a portion of the batch if the amount of pyro-Glu in the batch is within a predetermined range. Here too, the measuring step can employ any suitable method and units used to express the measured amount of pyro-Glu can be any suitable units (e.g., ppm or mole percent of chains). However the pyro-Glu is measured and whatever units are used to express the measured amount, the concentration of pyro-Glu in the selected batch is between 2000 and 7000 ppm (in some cases between 2500 and 6500 ppm) on a dry weight/dry weight basis.

A batch of a composition comprising an amino acid copolymer can be all or part of the product of a copolymer manufacturing process (e.g., all or part of a single manufacturing run). In some cases, one batch is analyzed. In some cases two or more batches are analyzed. In some cases, multiple samples taken from a single batch are analyzed. The composition containing a copolymer can be a drug substance (DS) (also known as an active pharmaceutical ingredient (API)), a drug product (DP), or a process intermediate. The copolymer can be glatiramer acetate.

Also described is a method for preparing a pharmaceutical composition comprising glatiramer acetate, comprising: polymerizing N-carboxy anhydrides of L-alanine, benzyl-protected L-glutamic acid, trifluoroacetic acid (TFA) protected L-lysine and L-tyrosine to generate a protected copolymer; treating the protected copolymer to partially depolymerize the protected copolymer, deprotect benzyl protected groups and deprotect TFA-protected lysines to generate glatiramer acetate; and purifying the glatiramer acetate, wherein the improvement comprises: measuring the amount of pyro-glutamate (pyro-Glu) in the purified glatiramer acetate. In other embodiments the improvement further comprises selecting the purified glatiramer acetate for use in the preparation of a pharmaceutical composition if the amount of pyro-Glu in the purified glatiramer acetate is within a predetermined range. In some embodiments the concentration of pyro-Glu in the selected purified glatiramer acetate 2000-7000 ppm or 2500-6500 ppm.

Also described is a method for preparing a pharmaceutical composition comprising glatiramer acetate, the method comprising: polymerizing N-carboxy anhydrides of L-alanine, benzyl-protected L-glutamic acid, trifluoroacetic acid (TFA) protected L-lysine and L-tyrosine to generate a protected copolymer; treating the protected copolymer to partially depolymerize the protected copolymer and deprotect benzyl protected groups and deprotecting TFA-protected lysines to generate glatiramer acetate; and purifying the glatiramer acetate, wherein the improvement comprises: measuring the amount of pyro-glutamate (pyro-Glu) during or after the polymerizing step.

Described herein is a method for preparing a pharmaceutical composition comprising glatiramer acetate, the method comprising: polymerizing N-carboxy anhydrides of L-alanine, benzyl-protected L-glutamic acid, trifluoroacetic acid (TFA) protected L-lysine and L-tyrosine to generate a protected copolymer; treating the protected copolymer to partially depolymerize the protected copolymer and deprotect benzyl protected groups and deprotecting TFA-protected lysines to generate glatiramer acetate; and purifying the glatiramer acetate, wherein the improvement comprises: measuring the amount of pyro-glutamate (pyro-Glu) during or after the partial depolymerization step.

In the aforementioned methods for preparing a pharmaceutical composition the improvement can further comprise: measuring the amount of pyro-glutamate (pyro-Glu) in the purified glatiramer acetate; selecting the purified glatiramer acetate for use in the preparation of a pharmaceutical composition if the amount of pyro-Glu in the purified glatiramer acetate is within a predetermined range; and preparing a pharmaceutical composition comprising at least a portion of the selected purified glatiramer acetate. In various embodiments, concentration of pyro-Glu in the selected purified glatiramer acetate is, for example, 2000-7000 ppm or 2500-6500 ppm.

Also described is a method for preparing a pharmaceutical composition comprising glatiramer acetate, comprising: polymerizing N-carboxy anhydrides of L-alanine, benzyl-protected L-glutamic acid, trifluoroacetic acid (TFA) protected L-lysine and L-tyrosine to generate a protected copolymer; treating the protected copolymer to partially depolymerize the protected copolymer and deprotect benzyl protected groups and deprotecting TFA-protected lysines to generate glatiramer acetate; and purifying the glatiramer acetate, wherein the improvement comprises: measuring the amount of benzyl alcohol during or after the polymerizing step, wherein the amount of benzyl alcohol is correlated to the amount of pyro-Glu.

Described herein is a method for preparing a pharmaceutical composition comprising glatiramer acetate, comprising: polymerizing N-carboxy anhydrides of L-alanine, benzyl-protected L-glutamic acid, trifluoroacetic acid (TFA) protected L-lysine and L-tyrosine to generate a protected copolymer; treating the protected copolymer to partially depolymerize the protected copolymer and deprotect benzyl protected groups and deprotecting TFA-protected lysines to generate glatiramer acetate; and purifying the glatiramer acetate, wherein the improvement comprises: measuring the amount of benzyl alcohol during or after the partial depolymerization step, wherein the amount of benzyl alcohol is correlated to the amount of pyro-Glu.

In either of the methods entailing measuring the amount of benzyl alcohol, the improvement can further comprise: measuring the amount of pyro-glutamate (pyro-Glu) in the purified glatiramer acetate; selecting the purified glatiramer acetate for use in the preparation of a pharmaceutical composition if the amount of pyro-Glu in the purified glatiramer acetate is within a predetermined range; and preparing a pharmaceutical composition comprising at least a portion of the selected purified glatiramer acetate. In various embodiments, the concentration of pyro-Glu in the selected purified glatiramer acetate is, for example, 2000-7000 ppm or 2500-6500 ppm.

The step of measuring the amount of pyro-Glu in a batch or sample can include any method for measuring (qualitatively or quantitatively) the amount of pyro-Glu and can include multiple steps and processes. Thus, the measuring step can include, for example: direct measurement of the copolymer, size fractionating the copolymer, digesting the copolymer, or cleaving the copolymer. The measuring can be based on, for example, the total amount of pyro-Glu or on the concentration of pyro-Glu or on the percentage of copolymer peptides that include a pyro-Glu. The measured amount can be expressed in any convenient units, e.g., in weight, weight percent or ppm (all measured in dry weight, i.e., total dry weight pyro-Glu in the sample/total dry weight of the sample), or mole percent of peptide chains. It should be noted that as the mole percent of chains and weight percent of chains are related by the average molecular weight of the copolymer, it is possible to interconvert between these values if the average molecular weight is known, estimated or assumed. However, the precise value of the calculated mole percent of chains will depend on whether the average molecular weight value used is a number average molecular weight (Mn), weight average molecular weight (Mw) or peak average molecular weight (Mp). While Mw, Mp or Mn can be used in the calculations, it is preferable to use Mn. Whatever method is used to measure pyro-Glu in the batch or sample, and whatever units are used to express the measured pyro-Glu in the batch or sample, the concentration of pyro-Glu in the selected batch is between 2000 and 7000 ppm (mass$_{pyro-Glu}$/mass$_{total}$)×10$^6$).

The methods can also include selecting the batch or pharmaceutical preparation as suitable for sale or administration to a human when the concentration of pyro-Glu in the batch is within a predetermined range, e.g., 2000-7000 ppm.

The measuring step can comprise providing a value (e.g., in units such as ppm, percent of peptide chains) for the amount of pyro-Glu in the batch and optionally comparing the value to a reference value (e.g., a specification for commercial release of a copolymer product).

Where the value for the amount of pyro-Glu in a batch of glatiramer acetate has a preselected relationship with the reference value, the method can include classifying, selecting, accepting, discarding, releasing, or withholding a batch of glatiramer acetate; reprocessing a batch through a previous manufacturing step; processing a batch of glatiramer acetate into drug product, shipping the product from a batch of glatiramer acetate, moving the batch of glatiramer acetate to a new location; or formulating, labeling, packaging, selling, offering for sell, or releasing a batch of glatiramer acetate into commerce.

Also described herein is a method of analyzing a composition comprising glatiramer acetate for the presence or amount of pyro-Glu, the method comprising: digesting a sample of the composition with a peptidase or protease (e.g., pyroglutamate amino peptidase, an endopeptidase, and trypsin), comparing the digestion products to a pyro-Glu reference standard, and evaluating the amount of pyro-Glu in the sample relative to the reference standard, thereby analyzing a composition comprising glatiramer acetate. In some cases the digestion products are separated by a chromatographic process prior to comparing the digestion to a pyro-Glu reference standard. Thus, the comparison step can include a chromatographic method (e.g., liquid chromatography, particularly HPLC) to separate components and mass spectrometry (MS) analysis or UV absorbance analysis to detect the amount of various components.

In some cases the step of measuring pyro-Glu in the batch comprises: digesting a sample with a peptidase or a protease; isolating pyro-Glu present in the digested sample; and measuring the amount of isolated pyro-Glu. The isolating step can comprise a chromatographic method (e.g., liquid chromatography, particularly HPLC). The measuring step can comprise mass spectrometry (MS) analysis or UV absorbance analysis The measuring step can comprise measuring UV absorbance (e.g., at 180-250 nm, 200 nm, or 210 nm). The isolating step can comprise a chromatographic method (e.g., liquid chromatography, particularly HPLC). The determining step can comprise mass spectrometry (MS) analysis. The isolating step can comprise HPLC and the measuring step can comprise UV absorbance analysis. The isolating step can comprise liquid chromatography and the measuring step can comprise mass spectrometry (MS) analysis.

In some cases, the pyro-Glu content of the copolymer or glatiramer acetate preparation is between 2000 to 7000 ppm, e.g., between 2500-6500 ppm, e.g., between 3000-6000 ppm, e.g., between 3300-4400 ppm. In some cases, the pyro-Glu content of the copolymer or glatiramer acetate preparation is less than 7000 ppm, e.g., less than 6000 ppm, less than 5000 ppm, less than 4000 ppm, less than 3000 ppm, or less than 2000 ppm.

As used herein, a "copolymer", "amino acid copolymer" or "amino acid copolymer preparation" is a heterogeneous mixture of polypeptides comprising a defined plurality of different amino acids (typically between 2-10, e.g., between 3-6, different amino acids). A copolymer may be prepared from the polymerization of individual amino acids. The term "amino acid" is not limited to naturally occurring amino acids, but can include amino acid derivatives and/or amino acid analogs. For example, in an amino acid copolymer comprising tyrosine amino acids, one or more of the amino acids can be a homotyrosine. Further, an amino acid copolymer having one or more non-peptide or peptidomimetic bonds between two adjacent residues is included within this definition. A copolymer is non-uniform with respect to the molecular weight of each species of polypeptide within the mixture.

DETAILED DESCRIPTION OF THE INVENTION

Other than molecular weight and amino acid composition, which are specified in the approved label for the product, the label and other available literature for Copaxone® does not provide detailed information about the physiochemical characteristics of the product. Based on detailed characterization of the product and process kinetics, the inventors have unexpectedly found a signature component of GA, L-pyro-Glutamic Acid (pyro-Glu) GA, that can be evaluated to assess the GA manufacturing process and product quality. In particular, evaluation of pyro-Glu content can identify differences in materials that are not observed by looking at molar mass and amino acid composition alone. By evaluating the pyro-Glu content of a sample of a copolymer, e.g., GA, one can identify non-conforming copolymer compositions. Accordingly, pyro-Glu content can be used to evaluate product and process quality for GA.

The production of GA entails both polymerization of amino acids and partial depolymerization of the resulting peptides. It has now been found that depolymerization is highly specific and non-stochastic and occurs to a disproportionately high extent to the N-terminal side of glutamate residues. Indirectly, this results in pyro-Glu GA as a signature structural characteristic of GA, surprisingly occurring primarily as a consequence of depolymerization. Pyro-Glu is present in GA in a range of 2000-7000 ppm and can be assessed to identify or evaluate GA and its method of manufacture, and/or to evaluate the quality or suitability of a GA product for pharmaceutical use.

Methods for Manufacture of Glatiramer Acetate

Generally, the process for the manufacture of glatiramer acetate includes three steps:

Step (1): polymerization of N-carboxy anhydrides of L-alanine, benzyl-protected L-glutamic acid, trifluoroacetic acid (TFA) protected L-lysine and L-tyrosine (collectively referred to as NCAs) to result in a protected copolymer, Step (2): depolymerization and benzyl deprotection of the protected copolymer using hydrobromic acid in acetic acid, and Step (3): deprotection of the TFA-protected lysines on the product copolymers followed by purification and drying of the isolated drug substance.

In Step (1) of the manufacturing method, the NCAs are co-polymerized in a predetermined ratio using diethylamine as an initiator. Upon consumption of the NCA components, the reaction mixture is quenched in water. The resulting protected polymer (Intermediate-1) is isolated and dried. In Step (2), the protected polymer (Intermediate-1) is treated with anhydrous 33% HBr in acetic acid (HBr/AcOH). This results in the cleavage of the benzyl protecting group on the glutamic acid as well as cleavage of peptide bonds throughout the polymer, resulting in a partially depolymerized product (Intermediate-2) with a reduced molecular weight relative to the parent Intermediate-1 polymer. After the reaction is quenched with cold water, the product polymer is isolated by filtration and washed with water. The Intermediate-2 material is dried before proceeding to Step (3). In Step (3), Intermediate-2 is treated with aqueous piperidine to remove the trifluoroacetyl group on the lysine. The resulting copolymer (Intermediate-3) is subsequently purified using diafiltration/ultrafiltration and the resulting acetate salt dried to produce Glatiramer Acetate drug substance.

Methods for the manufacture of glatiramer acetate have been described in the following publications: U.S. Pat. No. 3,849,550; WO 95/031990 and US 2007-0021324.

Process Chemistry of Synthetic Method and Structural Characterization of GA

By studying the polymerization/depolymerization chemistry using model peptide compounds to model the synthetic process for producing GA, the inventors have found that there are certain rules associated with the chemistry. By developing an understanding of these rules, it is apparent that GA is not a stochastic, or random, mixture of peptides. Rather, there are certain attributes that are conserved from batch-to-batch and can be measured in order to monitor and evaluate process and batch quality.

Figure 1:
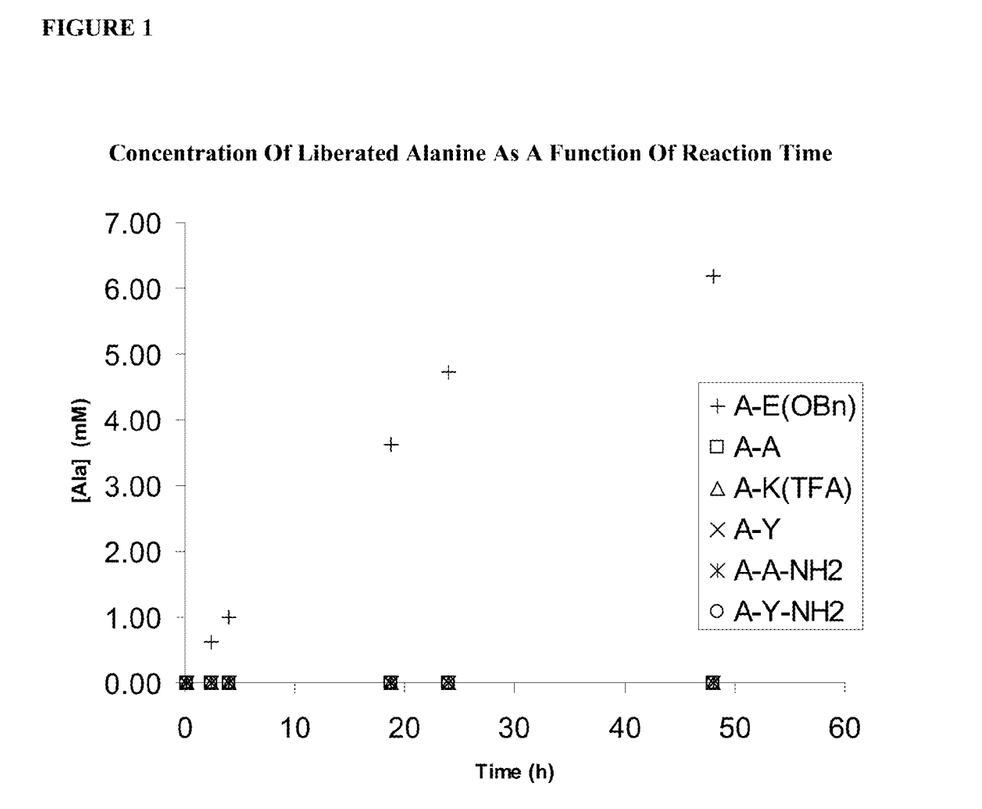
FIG. 1 shows release of alanine from dipeptides upon HBr/acetic acid treatment. A=Ala=Alanine; E=Glutamic Acid; K=Lysine; Y=Tyrosine. All dipeptides were prepared at a concentration of 10 mM. Two dipeptides (A-A-NH2 and A-Y—NH2) were amidated at the C-terminus.

Specifically, study of the kinetics of the depolymerization step of the GA manufacturing process using model peptide compounds revealed that Step 2 depolymerization occurs to disproportionately high levels on the N-terminal side of glutamate residues. In model compounds, the only appreciable cleavage was on the N-terminal side of glutamate residues (FIG. 1). In the manufacturing process of Glatiramer Acetate, cleavage occurs at all residues, but with a bias towards the N-terminal side of glutamate residues. Further, a modified amino acid, identified as pyro-glutamic acid (pyro-Glu), was found in tryptic peptides of Copaxone® samples. Analysis of aliquots removed from the depolymerization step at various time points and then further processed to produce GA revealed that the amount of pyro-Glu at amino termini increases as the depolymerization time increases. Thus, the level of pyro-Glu in the final GA product is surprisingly primarily a consequence of the depolymerization kinetics and is not accounted for solely by the polymerization chemistry. From this understanding of the chemistry of GA synthesis, and from characterization of the resulting product, it has thus been discovered that pyro-Glu is a signature structural characteristic of glatiramer acetate. The formation of pyro-Glu results from: (1) parameters relating to the polymerization reaction, as well as, surprisingly and unexpectedly, (2) parameters related to the de-polymerization reaction. Accordingly, pyro-Glu can be evaluated and monitored in the manufacture of GA (including in the final drug substance or drug product) in order to, e.g., (i) identify GA, (ii) assess the quality of GA (e.g., of a GA batch), and/or (iii) assess or confirm the quality of the GA manufacturing process.

Methods of Measuring Pyro-Glu

Because pyro-Glu is formed during the GA manufacturing process, its presence and level provide useful information regarding GA chemistry and product quality.

Certain methods are described herein for measuring pyro-Glu content in a composition that includes GA. However, it is understood that other methods to measure pyro-Glu can also be used.

One analytical method developed and described herein for the measurement of pyro-Glu content is based on enzymatic cleavage of an N-terminal pyroglutamate residue using pyro-glutamate aminopeptidase (e.g., from thermophilic archaebacteria, *Pyrococcus furiosus*). The amount of pyro-Glu in the resulting enzymatic hydrolysate can be analyzed by a suitable technique, such as reverse phase liquid chromatography, to determine the ppm or w/w % of pyro-Glu in a GA sample. This method does not require knowing the mean chain length or average molecular weight of the GA in the composition. Accordingly, ppm or w/w % of pyro-Glu is a preferred expression of the amount of pyro-Glu in a batch or a sample of copolymer, e.g., GA.

Various methods can be used to determine the percentage of peptide chains bearing pyro-Glu in a GA sample. A determination of mole % or percent of chains bearing pyro-Glu requires a determination of average molecular size or mean chain length. Molecular size can be evaluated e.g., by SEC MALLS (size exclusion chromatography with multiple angle laser light scattering). Mean chain length can be computed e.g., by labeling (e.g., with a radioactive or fluorescent label) the free amino termini with a molecule which can be directly quantified. One analytical method developed and described herein for measuring the percentage of peptide chains bearing pyro-Glu involves combining quantitative Edman degradation with enzymatic removal of pyro-Glu. Such an analysis can entail: 1) quantifying the N-terminal amino acids in a sample of GA before treatment to remove pyro-Glu; and 2) quantifying the N-terminal amino acids in a sample of GA after treatment to remove pyro-Glu.

EXAMPLES

Example 1

Depolymerization Kinetics of Glatiramer Acetate Method of Manufacture

To investigate the depolymerization kinetics, the reaction of various dipeptide model compounds with HBr/AcOH was investigated. FIG. 1 shows release of alanine from dipeptides upon HBr/acetic acid treatment as performed in Step 2 of the manufacturing process. All dipeptides were prepared at a concentration of 10 mM. Two dipeptides (A-A-NH2 and A-Y—NH2) were amidated at the C-terminus. As shown in FIG. 1, release of alanine was only observed for A-E(OBn), indicating that dipeptides with Glu(OBn) in the C-terminal position demonstrate the most cleavage over the course of 24-48 h reaction times as compared to dipeptides without Glu in the C-terminal position. Thus, depolymerization occurs to an appreciable extent only on the N-terminal side of glutamate residues in these model systems. In the actual manufacturing process for Glatiramer Acetate, cleavage occurs at all residues, but still shows a strong bias for the N-terminal side of glutamate residues.

Example 2

Presence of N-Terminal Pyro-Glu Structures

Figure 2:
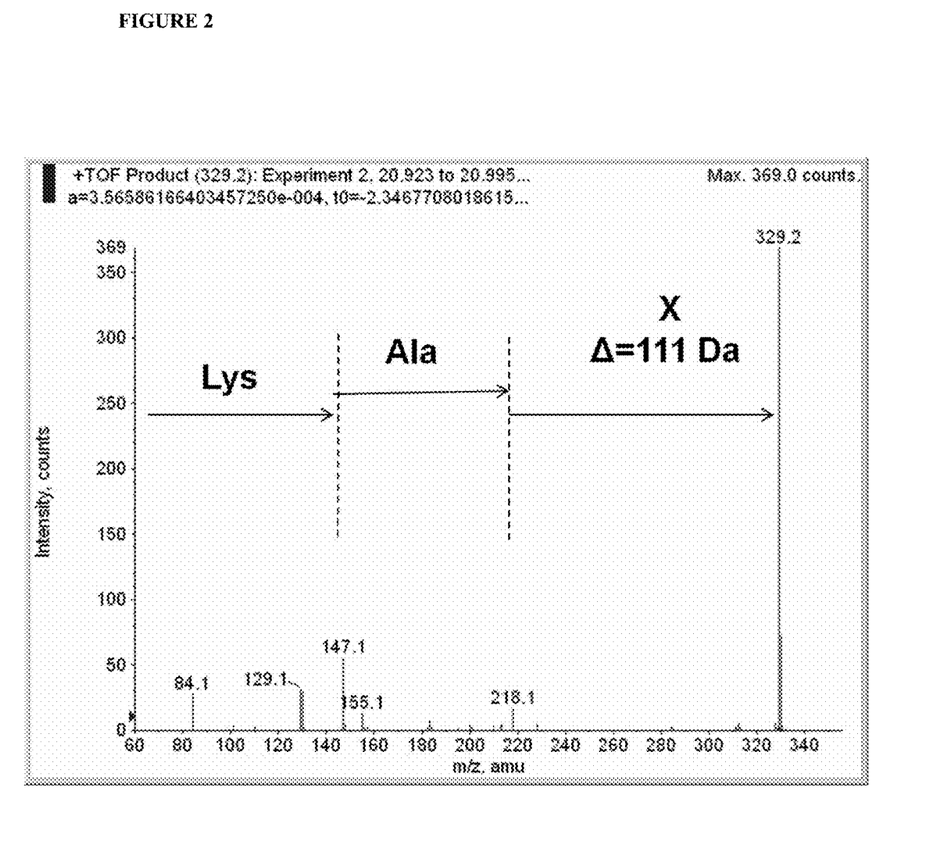
FIG. 2 is an LC-MS trace showing an unusual amino acid with residual mass of 111 Da ("X") at the N-terminus of a peptide derived from trypsin-digested Copaxone®. Lys=Lysine; Ala=Alanine.
Figure 3:
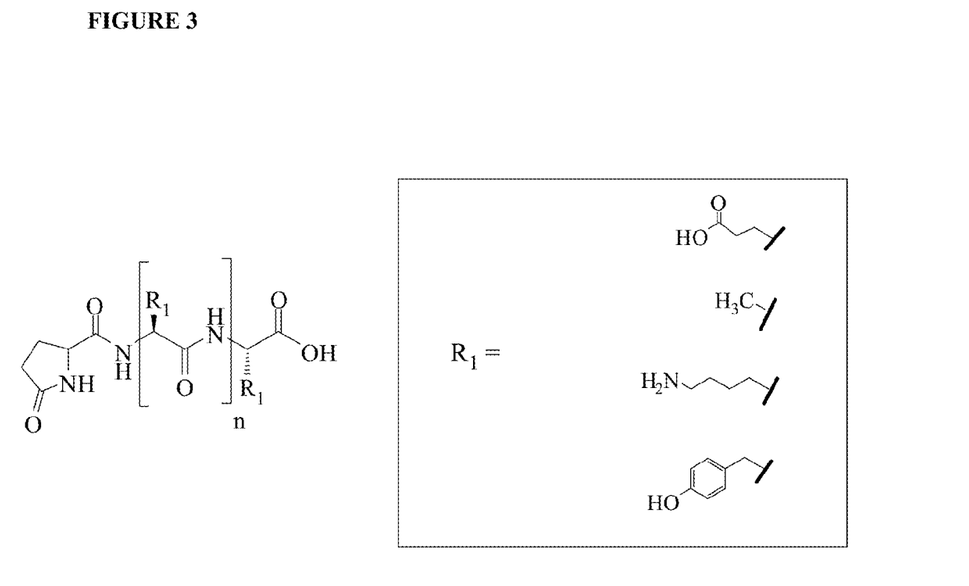
FIG. 3 shows the structure of L-pyro Glutamic Acid (pyro-Glu) Glatiramer Acetate (GA).

Trypsin digestion of Copaxone® followed by LC-MS analysis identified expected peptides containing each of the amino acids A, E, K and Y. In addition, unexpected peptides were also found. An unusual amino acid (m/z 111) with residual mass of 111 Da was observed at the N-terminus of several such unexpected peptides derived from trypsin-digested Copaxone® (labeled as "X", FIG. 2). From LC-MS/MS analysis it was determined that the unusual amino acid is pyro-Glu, formed by cycling of N-terminal glutamic acid to form pyro-glutamic acid losing a water molecule [111 Da=129 Da (Glutamic acid residue)−18 Da (H2O)]. FIG. 3 shows the structure of L-pyro Glutamic Acid (pyro-Glu) GA.

Example 3

Evaluation of Pyro-Glu Content on a Weight Basis

This example describes a method for evaluating pyro-Glu content in a copolymer composition.

An analytical method developed for the pyro-glutamate content assay is based on enzymatic cleavage of a N-terminal pyro-glutamate residue using pyro-glutamate aminopeptidase (from thermophilic archaebacteria, *Pyrococcus furiosus*). Pyro-glutamate in the resulting enzymatic hydrolysate is isolated by reverse phase liquid chromatography followed by detection at 200 nm using a reference standard curve prepared with known concentrations of L-Pyro-glutamate. Neurotensin (a commercially available polypeptide having 100% pyro-glutamate at the N-terminus) is assayed as a control to ensure the acceptability of the digestion and adequacy of the HPLC separation. The chromatographic analysis is performed using a Waters Atlantis C18 HPLC column and an isocratic mobile phase consisting of 100% Water, adjusted to pH 2.1 with phosphoric acid. Samples and Standards are held at 2-8° C. The peak corresponding to the pyro-glutamate moiety elutes at a retention time of approximately 12 minutes. The direct measure of pyro-glutamate content is on a w/w basis and the results are expressed as ppm (microgram/gram).

Example 4

Evaluation of Pyro-Glu Content on a Percentage of Peptide Chains Basis

The percentage of peptide chains in a sample of GA bearing pyro-Glu can be measured as an alternative to measuring the amount of pyro-Glu in a sample of GA. The percentage of peptide chains bearing pyro-Glu can be determined by combining quantitative Edman degradation with enzymatic removal of pyro-Glu. Thus, the analysis entails: 1) quantifying the N-terminal amino acids in a sample of GA before treatment to remove pyro-Glu; and 2) quantifying the N-terminal amino acids in a sample of GA after treatment to remove pyro-Glu.

An Edman degradation reaction was used to quantify the N-terminal amino acids in a sample of GA before and after treatment with pyroglutamate aminopeptidase (PA) to remove pyro-Glu. This reaction was performed manually to avoid quantitative limitations of automatic N-terminal peptide sequencers. The results of this analysis are presented in the table below.

TABLE 1

N-terminal Amino Acid

| Amino Acid | nmol N-terminal amino acid | |
|---|---|---|
| | Before PA Treatment (st. dev) | After PA Treatment (st. dev) |
| Ala | 25.1 (0.6) | 51.7 (0.5) |
| Glu | 7.8 (0.3) | 15.7 (0.1) |
| Lys | 9.0 (0.2) | 20.2 (0.8) |
| Tyr | 6.5 (0.1) | 10.5 (0.2) |
| Total | 48.4 | 98.1 |

As can be seen in Table 1, above, the N-terminal amino acid concentration increased from 48.4 to 98.1 nmol after PA treatment. This is because removal of pyro-Glu permits detection of peptides that could not previously have been detected by Edman degradation. The percentage of chains bearing pyro-Glu can be calculated as follows: % chains capped by pyroglutamate=(Pafter−Pbefore)/Pafter×100%. In this calculation, Pbefore and Pafter are the concentrations of N-terminal amino acids with and without PA treatment, respectively. In this example, 51% of the polymer chains were capped by pyroglutamate.

Example 5

Pyro-Glu Content can Distinguish Glatiramer Acetate

Using the method described in Example 3, the pyro-Glu content of commercial Copaxone® was compared to several other copolymer samples. A sample of glatiramer acetate (M-GA) prepared according to the method described in U.S. Pat. No. 3,849,550 was evaluated for pyro-Glu content. Table 2, below, provides the results of the analysis of a number of compositions, this sample conforms to the range found for pyro-Glu content from a sampling of Copaxone® lots, or between 2500-6500 ppm.

TABLE 2

Analysis of Samples
Analysis of Samples

| Sample | Molecular weight (Mp) (Da) | Amino acid composition (avg. molar fraction)[2] | P-Glu content (ppm) |
|---|---|---|---|
| Copaxone ® | 5,000-9,000[1] | 0.141 L-Glutamic acid<br>0.427 L-alanine<br>0.095 L-tyrosine<br>0.338 L-lysine | 2500-6500 ppm[4] |
| Glatiramer acetate sample (M-GA) | 8407 (conforms) | (conforms)[3] | 4900 ppm (conforms) |
| Deviating sample A | 6579 (conforms) | (conforms)[3] | 8200 ppm (fails) |
| Deviating sample B | 4808 (fails) | (conforms)[3] | 7500 ppm (fails) |

[1]Molecular weight range specified in Copaxone ® product label and prescription information
[2]Average molar fraction target specified in Copaxone ® product label and prescription information
[3]Conforms relative to specification range based on label target plus allowance for manufacturing and measurement variability
[4]Range is 75%/125% of Copaxone min/max for 30 commercial samples To test the ability of pyro-Glu content to distinguish glatiramer acetate from non-conforming copolymers, two control copolymers were tested. The control copolymers were made with deliberate and specific deviations in the timing of NCA addition or in the duration of step 2. As shown in Table 1, both deviating samples A and B were outside of the range for pyro-Glu content determined for Copaxone®. Sample A was within the range for Copaxone® molar mass and amino acid composition while Sample B failed molar mass but conformed in amino acid composition. This data shows that evaluation of pyro-Glu content can identify differences in materials and process not observed by looking at molar mass and amino acid composition alone and illustrates the ability of pyro-Glu measurement to identify non-conforming copolymer. Accordingly, pyro-Glu content can be used to evaluate product and process quality for glatiramer acetate.

What is claimed is:

1. A method for manufacturing a pharmaceutical composition comprising glatiramer acetate, the method comprising:
preparing an amino acid copolymer of L-glutamic acid, L-alanine, L-lysine, and L-tyrosine, wherein the preparing step comprises co-polymerizing N-carboxy anhydrides of L-alanine, benzyl-protected L-glutamic acid, trifluoroacetic acid (TFA)-protected L-lysine, and L-tyrosine to generate a first material; treating the first material to deprotect the benzyl-protected L-glutamic acid therein and to partially depolymerize the first material, thereby generating a second material; treating the second material to deprotect the TFA-protected L-lysine to produce a third material; and purifying the third material, to thereby produce the copolymer of L-glutamic acid, L-alanine, L-lysine, and L-tyrosine;
measuring pyro-glutamate content of the copolymer in a sample of the copolymer;
measuring the peak average molecular weight (Mp) of the copolymer;
processing the copolymer to produce a pharmaceutical composition comprising glatiramer acetate only if the measured pyro-glutamate content of the copolymer in the sample is within 2000-7000 parts per million (ppm) on a dry weight/dry weight basis,
thereby producing a pharmaceutical composition comprising glatiramer acetate.

2. The method of claim 1 wherein: the step of deprotecting the TFA-protected L-lysine comprises treating the second material with aqueous piperidine.

3. The method of claim 1, wherein co-polymerizing N-carboxy anhydrides of L-alanine, benzyl-protected L-glutamic acid, trifluoroacetic acid (TFA)-protected L-lysine, and L-tyrosine to generate a first material comprises contacting the N-carboxy anhydrides of L-alanine, benzyl-protected L-glutamic acid, trifluoroacetic acid (TFA)-protected L-lysine, and L-tyrosine with diethylamine.

4. The method of claim 2, wherein co-polymerizing N-carboxy anhydrides of L-alanine, benzyl-protected L-glutamic acid, trifluoroacetic acid (TFA)-protected L-lysine, and L-tyrosine to generate a first material comprises contacting the N-carboxy anhydrides of L-alanine, benzyl-protected L-glutamic acid, trifluoroacetic acid (TFA)-protected L-lysine, and L-tyrosine with diethylamine.

5. The method of claim 1, wherein treating the first material to deprotect the benzyl-protected L-glutamic acid therein and to partially depolymerize the first material comprises treating the first material with anhydrous 33% HBr in acetic acid.

6. The method of claim 2, wherein treating the first material to deprotect the benzyl-protected L-glutamic acid therein and to partially depolymerize the first material comprises treating the first material with anhydrous 33% HBr in acetic acid.

7. The method of claim 3, wherein treating the first material to deprotect the benzyl-protected L-glutamic acid therein and to partially depolymerize the first material comprises treating the first material with anhydrous 33% HBr in acetic acid.

8. The method of claim 1, wherein measuring pyroglutamate content of the copolymer in a sample of the copolymer comprises obtaining a sample of a manufacturing batch of the copolymer.

9. The method of claim 2, wherein measuring pyroglutamate content of the copolymer in a sample of the copolymer comprises digesting the copolymer in the sample with pyroglutamate aminopeptidase.

10. The method of claim 1, wherein measuring pyroglutamate content comprises determining the ppm on a dry weight/dry weight basis of pyro-Glu in the sample of the copolymer.

11. The method of claim 1, further comprising packaging, labeling, or releasing into commerce the pharmaceutical composition comprising glatiramer acetate.

12. The method of claim 1, further comprising offering for sale or selling the pharmaceutical composition comprising glatiramer acetate.

13. The method of claim 1, further comprising shipping or moving to a new location the pharmaceutical composition comprising glatiramer acetate.

14. The method of claim 1, wherein the glatiramer acetate has an Mp of 5000-9000 Da.

\* \* \* \* \*